US00PP08584P

United States Patent [19]

Stravers

[11] Patent Number: Plant 8,584

[45] Date of Patent: Feb. 8, 1994

[54] GERBERA PLANT "TEROPTIMA"

[75] Inventor: Lambertus J. M. Stravers, Kudelstaart, Netherlands

[73] Assignee: Terra Nigra B.V., De Kwakel, Netherlands

[21] Appl. No.: 942,275

[22] Filed: Sep. 9, 1992

[30] Foreign Application Priority Data

Dec. 10, 1990 [NL] Netherlands ..... GRB 1191

[51] Int. Cl.[5] ..... A01H 5/00

[52] U.S. Cl. ..... Plt./68.1

[58] Field of Search ..... Plt. 68.1

*Primary Examiner*—James R. Feyrer
*Assistant Examiner*—Elizabeth C. Kemmerer

[57] ABSTRACT

A new and distinct cultivar of Gerbera plant named 'Teroptima', characterized by its single type, a unique pink ray floret which fades to white toward the center, a red-purple disc floret the outer petaloids of which fade to white, pink perianth lobe color and 120 mm overall flower diameter is disclosed.

1 Drawing Sheet

BACKGROUND OF THE INVENTION

The present invention comprises a new and distinct cultivar of *Gerbera Jamesonni,* referred to by the cultivar name 'Teroptima'. 'Teroptima' was originated from a hybridisation program in De Kwakel, The Netherlands in 1988. The female parent was 'Terfame' (registration number 7455; Jun. 10, 1986), and the male parent was unnamed seedling 87.241. The female parent 'Terfame' has a yellow color without a black center. Production of flowers, vase-life, and diameter of 'Terfame' and 'Teroptima' are identical. 'Terfame' has been available outside Terra Nigra, but has not been patented in the USA. The male parent 87.241 has about the same production of flowers and diameter as 'Teroptima'; however, the color pink of 87.241 is more clear and has a dark heart. 87.241 has not been available outside Terra Nigra. The new cultivar was selected by me from the progeny of the stated parentage on or about October 1988. The first asexual reproduction of 'Teroptima' was accomplished when vegetative cuttings were taken on April 1989 in De Kwakel. The new cultivar is presently being propagated by cuttings and tissue culture. Horticultural examination of selected units initiated November 1989 has demonstrated that the combination of characteristics as herein disclosed for 'Teroptima' are firmly fixed and are retained through successive generations of asexual reproduction.

The following observations, measurements and comparisons describe plants grown in De Kwakel, The Netherlands, under greenhouse conditions which closely approximate those generally used in commercial practice. The following traits have been repeatedly observed and are determined to be basic characteristics of *Teroptima',* which in combination distinguish this Gerbera plant from its parents and all other varieties of which I am aware:

1. Type: Single.
2. Color of ray floret: Very distinct pink.
3. Color of disc floret: Distinct red-purple.
4. Color of perianthy lobe: Pink.
5. Diameter of flower head: medium/large 120 mm.

Of the many commercial cultivars known to me, there is no cultivar similar in comparison to 'Teroptima'.

BRIEF DESCRIPTION OF THE FIGURE OF THE DRAWING

The accompanying photographic drawing shows typical inflorescence and foliage characteristics nearly true as possible. In the following description, color references are made to the Royal Horicultural Society Colour Chart (RHS). The color values were determined at 11:00 a.m. on Oct. 12, 1990 under natural light at De Kwakel.

BOTANICAL DESCRIPTION OF THE PLANT

Botanical: *Gerbera jamessonii* cv Teroptima.

1. INFLORESCENCE

A. Capitulum:
- *Form.*—Cup shaped.
- *Type.*—Single.
- *Diameter across face.*—120 mm.

B. Corolla of ray florets:
- *Color (general tonality from a distance of 3 meters).*—Pink.
- *Color (topside).*—RHS 49C.
- *Color (bottom).*—RHS 36D.

C. Corolla of disc florets:
- *Color (mature).*—Purple RHS 187A.
- *Color (immature).*—Purple RHS 187A.

D. Reproductive organs:
- *Stigma.*—White RHS 155B.
- *Anthers.*—Dark yellow RHS 14A.
- *Pappus.*—Yellow RHS 11C.

PLANT

A. General appearance:
- *Height.*—40–45 cm.

B. Foliage:
- *Color (abaxial).*—RHS 146A.
- *Color (adaxial).*—RHS 147B.
- *Shape.*—The angle of apex: Right angle. The shape of apex: Pointed. The margin of lobes: Sinuate.

C. Disease resistance: No special resistance.

3. OTHER CHARACTERISTICS

The following traits have been repeatedly observed and are determined to be basic characteristics of 'Teroptima', which in combination distinguish this Gerbera as a new and distinct cultivar.

Leaf blade:

*Length.*—Medium (55 cm).

*Width.*—Medium (20 cm).

*Thickness.*—Medium.

*Blistering.*—Weak.

*Pubescence.*—On upper side (midrib excluded) of the leaf blade is medium.

*Depth of cuts or incisions in leaf.*—Basal part: Deep. Central part: Medium. Distal part: Shallow.

*Color.*—Upperside of the leaf blade is medium green (RHS 146A).

*Glossiness on upper side.*—Medium.

*Angle of apex.*—Right angle.

*Shape of apex.*—Pointed.

*Margin of lobes.*—Sinuate.

*Extensions of margin.*—Small.

*Petiole length.*—Medium.

*Petiole anthocyanin coloration.*—Present.

Peduncle:

*Length.*—Medium (65 cm).

*Cross section.*—Elliptic.

*Tendency to fasciation.*—Present.

*Thickness.*—Medium.

*Strength.*—Strong.

*Pubescence.*—Medium.

*Color.*—Medium green.

*Anthocyanin coloration.*—At base: Medium. At top: Absent. *Involucral bracts.*—Absent.

Flower head:

*Type.*—Single.

*Diameter.*—Medium (approx. 120 mm).

*Involucre.*—Height: Medium (14 mm). Diameter: Medium. Number of bracts: Medium (54). Longitudinal axis of bracts of inner rows: Reflexing. Anthocyanin: Present. Pubescence: Medium.

*Ray florets.*—Number: Medium (55). Shape: Narrow obovate. Longitudinal axis outer row: Incurving. Logitudinal axis inner row: Incurving.

*Outer ray florets.*—Cross section: Incurving. Length: Medium (58 mm). Width: Medium. Longitudinal folding: Medium. Angle of apex: Right. Shape of apex: Rounded. Incisions of apex: Present. Number: Two. Depth: Deep. Length of free petals: Short. Color distribution on inner side: Lighter towards base. Edge of different color: Absent. Striation: Absent. Claw spot: Present.

Disc florets:

*Diameter.*—Medium.

*Main color perianth lobes.*—Pink for both female (RHS 62D) and male flowers (RHS 62B).

Reproductive parts:

*Stigma.*—Main color white (RHS 155B).

*Anthers.*—Main color dark yellow (RHS 14A). Color of top relative to other parts is lighter. Longitudinal striping: Present.

*Pappus.*—Main color yellow (RHS 11C). Color on top relative to other parts is darker. Orientation: Level of top relative to closed disc florets is above.

*Fertility.* Very good; about 200 pollen. The plant will form viable seed easily.

I claim:

1. A new and distinct cultivar of Gerbera plant named 'Teroptima', as illustrated and described, characterized by its single type, a unique pink ray floret which fades to white toward the center, a red-purple disc floret the outer petaloids of which fade to white, pink perianth lobe color and 120 mm overall flower diameter.

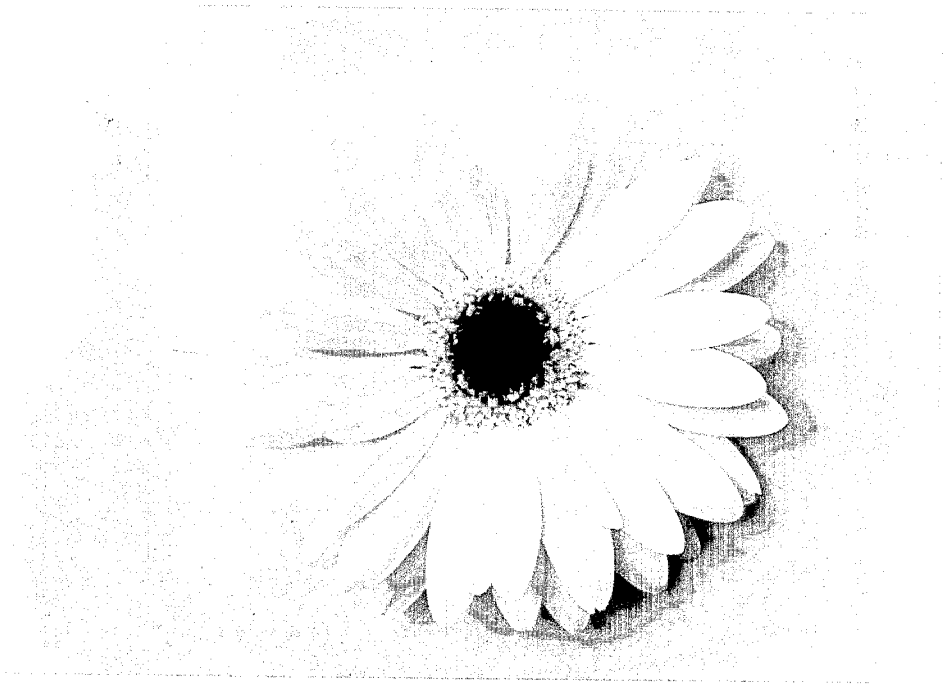

* * * * *